United States Patent
Linker

(10) Patent No.: US 7,630,756 B2
(45) Date of Patent: Dec. 8, 2009

(54) LONG-TERM MONITORING FOR DETECTION OF ATRIAL FIBRILLATION

(75) Inventor: David Thor Linker, Seattle, WA (US)

(73) Assignee: University of Washington, Seattle, WA (US)

( * ) Notice: Subject to any disclaimer, the term of this patent is extended or adjusted under 35 U.S.C. 154(b) by 368 days.

(21) Appl. No.: 11/253,375

(22) Filed: Oct. 19, 2005

(65) Prior Publication Data
US 2006/0084883 A1 Apr. 20, 2006

Related U.S. Application Data

(60) Provisional application No. 60/620,598, filed on Oct. 19, 2004.

(51) Int. Cl.
*A61B 5/0452* (2006.01)
(52) U.S. Cl. .................. 600/509; 600/515
(58) Field of Classification Search ............ 600/509, 600/515–519
See application file for complete search history.

(56) References Cited

U.S. PATENT DOCUMENTS

| | | | |
|---|---|---|---|
| 5,348,008 A | 9/1994 | Bornn et al. | |
| 6,487,442 B1 | 11/2002 | Wood | |
| 6,701,183 B2 | 3/2004 | Baker et al. | |
| 2002/0052557 A1 | 5/2002 | Griffin et al. | |
| 2002/0147409 A1 | 10/2002 | Baker et al. | |
| 2002/0151806 A1* | 10/2002 | Starobin et al. | 600/509 |
| 2003/0130586 A1 | 7/2003 | Starobin et al. | |
| 2006/0089559 A1* | 4/2006 | Barbieri et al. | 600/509 |

FOREIGN PATENT DOCUMENTS

| | | |
|---|---|---|
| EP | 1 219 237 A2 | 7/2002 |
| WO | 02/056961 A2 | 7/2002 |
| WO | 03/105020 A2 | 12/2003 |

OTHER PUBLICATIONS

Ang, N.H., "Real-Time Electrocardiogarm Signal Processing for Atrial Fibrillation Detection," Final Report of the Post-Masters Program: Mathermatics for Industry, Stan Ackermans Institute, Eindhoven University of Technology, Netherlands, 2004, 53 pages.

(Continued)

*Primary Examiner*—George R Evanisko
*Assistant Examiner*—Joseph M Dietrich
(74) *Attorney, Agent, or Firm*—Christensen O'Connor Johnson Kindness PLLC

(57) ABSTRACT

A method and a system for detection of an arrhythmia, the method comprising determining a number of heart beat intervals; determining an instantaneous heart rate for each of the heart beat intervals; determining the variability of the instantaneous heart rates compared to a mean of the number of instantaneous heart rates; determining a non-linear value that represents the variability of the instantaneous heart rates; and detecting the arrhythmia by comparing the non-linear value with a predetermined threshold.

12 Claims, 11 Drawing Sheets

OTHER PUBLICATIONS

Bassingthwaighte, J.B., and G.M. Raymond, "Evaluation of the Dispersional Analysis Method for Fractal Time Series," *Annals of Biomedical Engineering* 23(4):491-505, 1995.

Duverney, D., et al., "High Accuracy of Automatic Detection of Atrial Fibrillation Using Wavelet Transform of Heart Rate Intervals," *Pacing and Clinical Electrophysiology* 25(4, Part 1):457-462, April 2002.

"Geratherm Awarded Licence for Cardio Monitor," Geratherm Medical AG, May 26, 2004, <http://www.geratherm.com/en/iv_pressmitteilungen>, [retrieved Jan. 26, 2006].

"How It Works," ©2002 CardioNet, <http://www.cardionet/how.html>[retrieved Jan. 26, 2006].

*Instromedix, A Card Guard Company*, ©2004 Card Guard® Group of Companies, <http://www.instromedix.com> [retrieved Jan. 26, 2006].

Israel, C.W., et al., "Long-Term Risk of Recurrent Atrial Fibrillation as Documented by an Implantable Monitoring Device: Implications for Optimal Patient Care," *Journal of the American College of Cardiology* 43(1):47-52, 2004.

Page, R.L., et al., "Asymptomatic or 'Silent' Atrial Fibrillation: Frequency in Untreated Patients and Patients Receiving Azimilide," *Circulation* 107(8):1141-1145, 2003.

Swerdlow, C.D., et al., "Detection of Atrial Fibrillation and Flutter by a Dual-Chamber Implantable Cardioverter-Defibrillator," *Circulation* 101(8):878-885, 2000.

Tatano, K., and L, Glass, "Automatic Detection of Atrial Fibrillation Using the Coefficient of Variation and Density Histograms of RR and $\Delta\Delta$RR Intervals," *Medical and Biological Engineering and Computing* 39(6):664-671, 2001.

Wolk, R., et al., "The Incidence of Asymptomatic Paroxysmal Atrial Fibrillation in Patients Treated With Propranolol or Propafenone," *International Journal of Cardiology* 54(3):207-211, 1996.

Malik, M., "Heart Rate Variability. Standards of Measurement, Physiological Interpretation, and Clinical Use," European Heart Journal 17(3):354-381, Mar. 1996.

Partial European Search Report mailed Sep. 28, 2009, issued in European Application No. 05809951.6, filed Oct. 19, 2005.

* cited by examiner

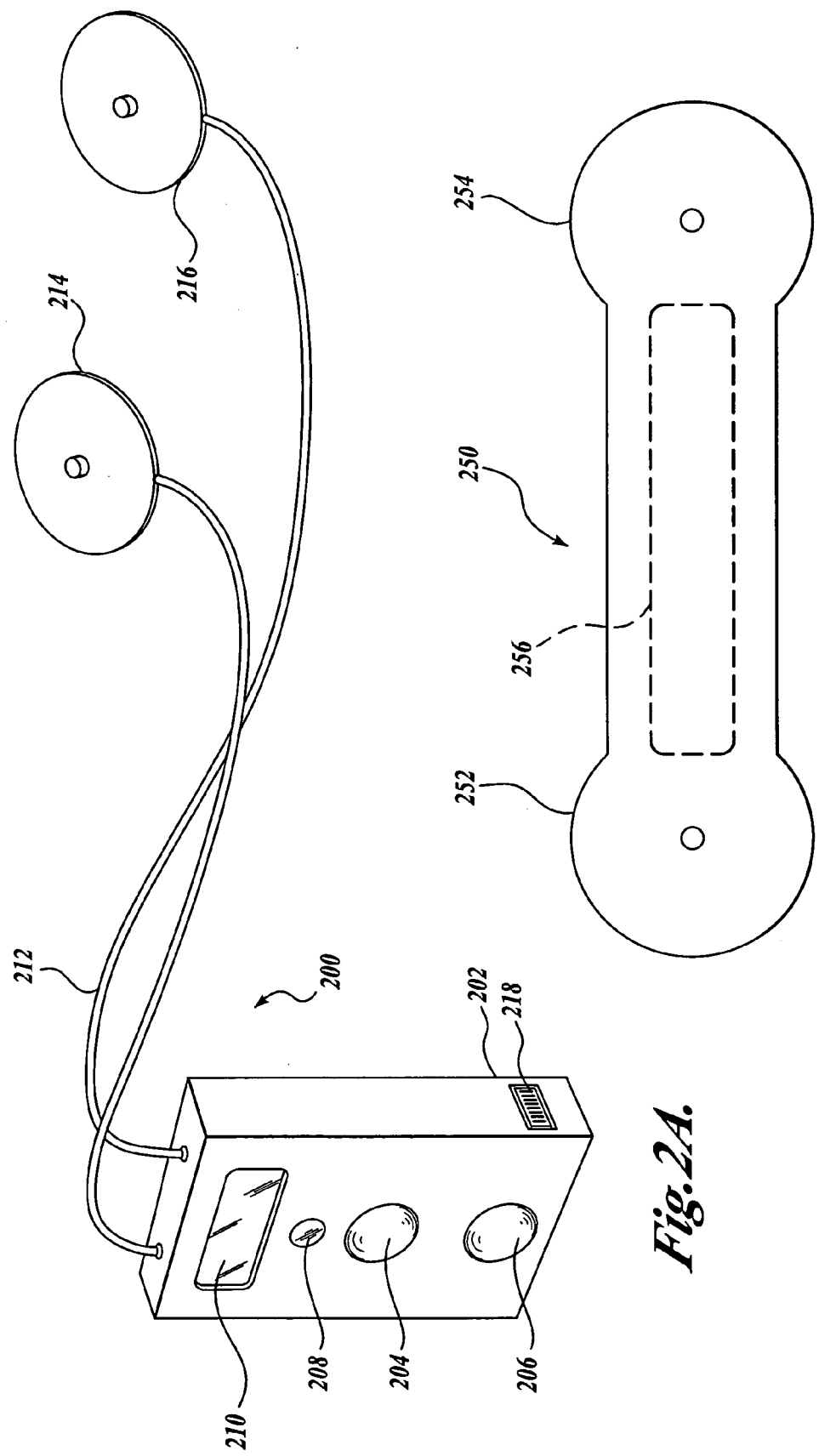

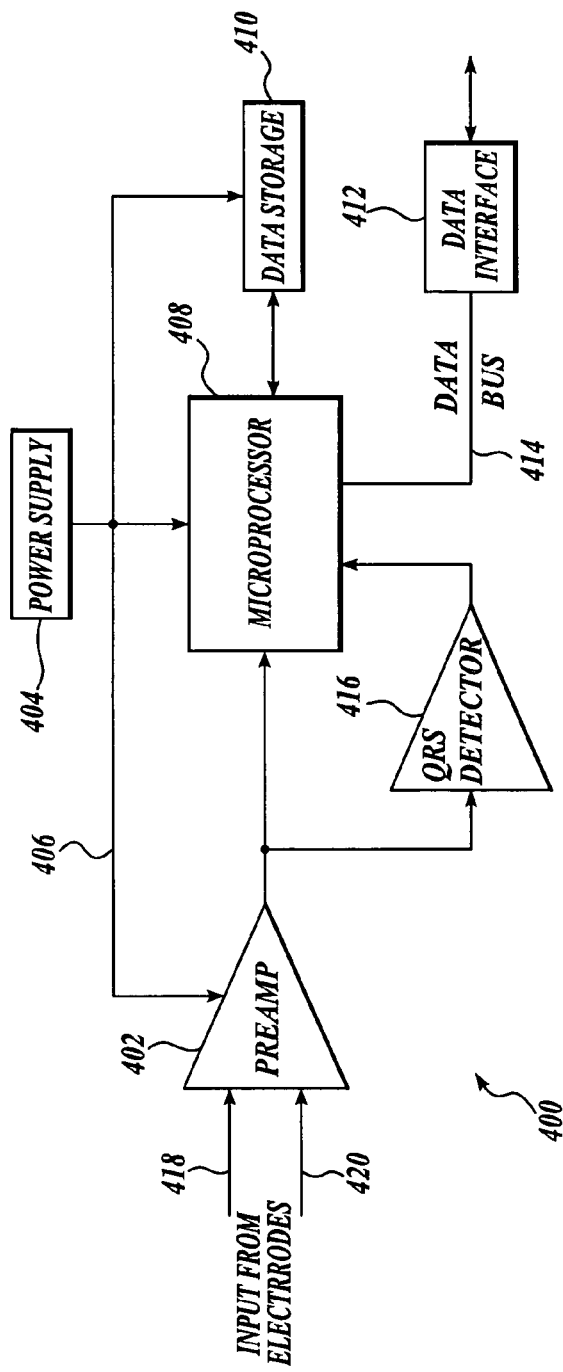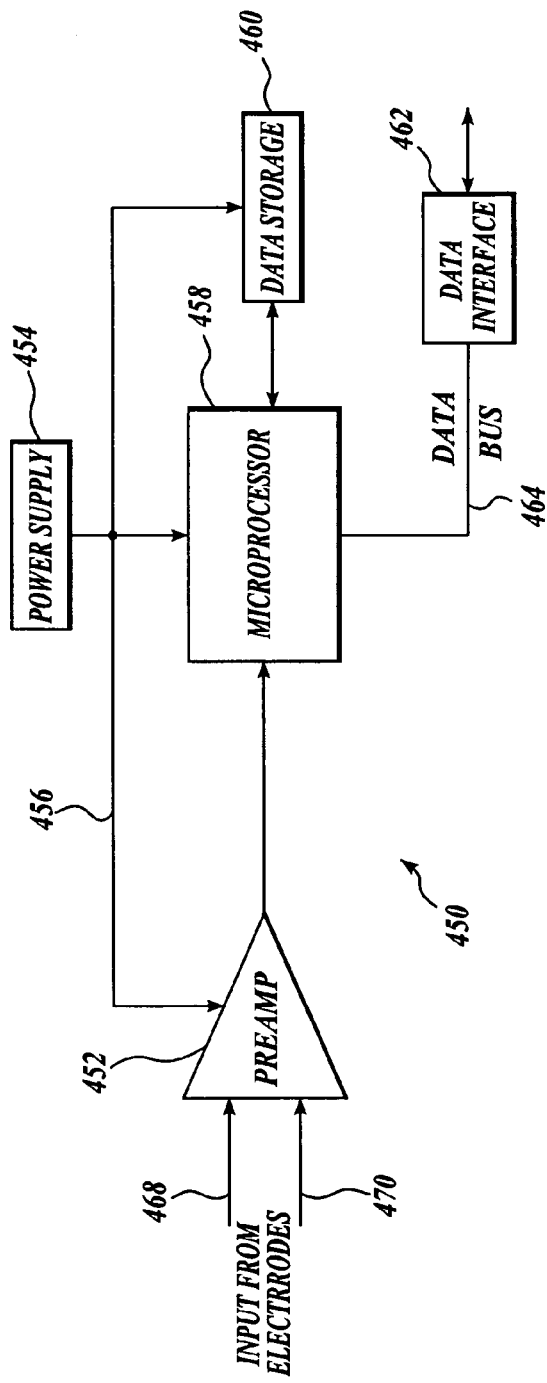

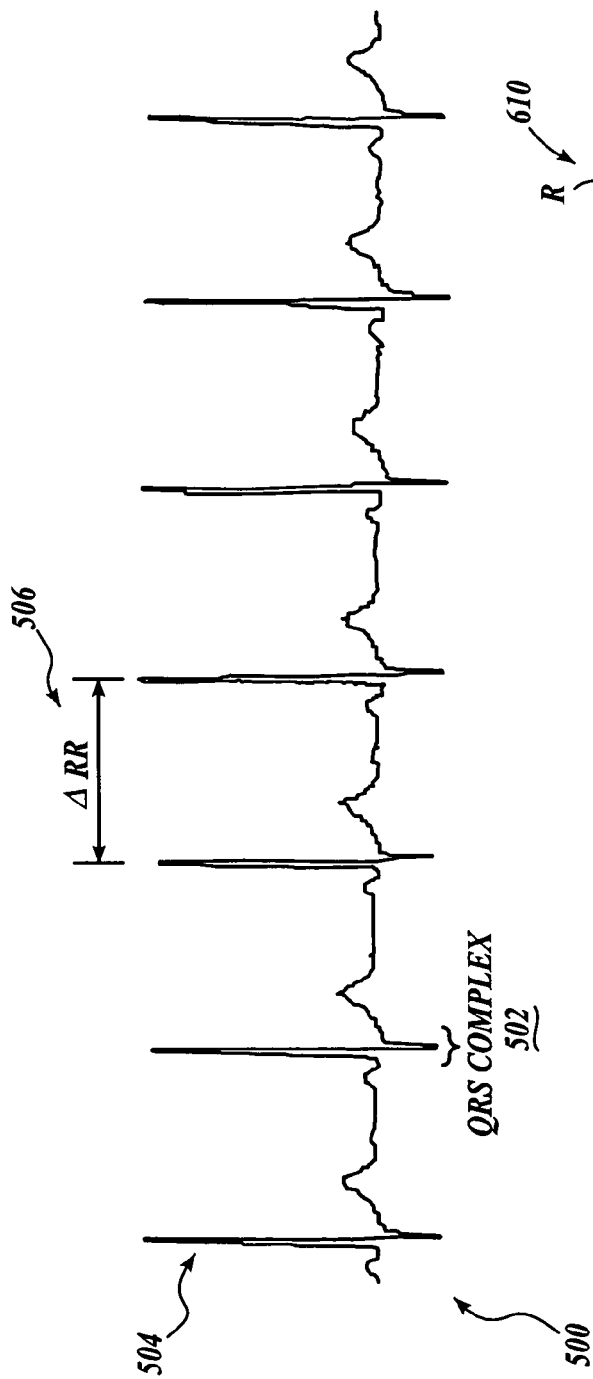
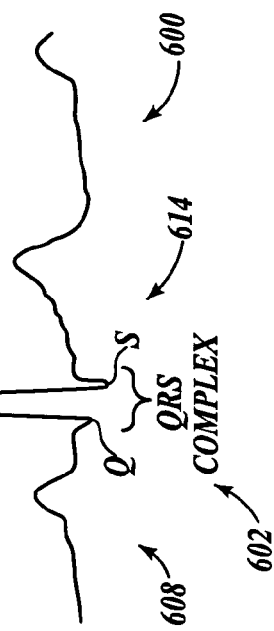
Fig. 5.
Fig. 6.

LONG-TERM MONITORING FOR DETECTION OF ATRIAL FIBRILLATION

CROSS-REFERENCE(S) TO RELATED APPLICATION(S)

This application claims the benefit of U.S. Provisional Application No. 60/620,598, filed Oct. 19, 2004, the disclosure of which is hereby expressly incorporated by reference, and the filing date of which is hereby claimed under 35 U.S.C. § 119(e).

FIELD OF THE INVENTION

The present invention relates to monitoring and detection of rhythm disturbance of the heart, and more specifically to a method and system for long-term monitoring and detection of atrial fibrillation.

BACKGROUND OF THE INVENTION

Atrial fibrillation ("AF") is a very common rhythm disturbance of the heart which affects a significant proportion of the general population and is associated with increased risk of stroke and death. Currently, atrial fibrillation is diagnosed by symptoms or is discovered incidentally. Available evidence indicates that a significant portion of patients with atrial fibrillation do not have symptoms, and consequently the atrial fibrillation of such patients may not be discovered during routine medical examinations. However, atrial fibrillation may be diagnosed using medical equipment, such as rhythm monitors. Monitoring techniques used by available rhythm monitors include monitoring the heart rhythm for a short period of time or monitoring intermittently. Unfortunately, these monitoring techniques have low sensitivity for the detection of atrial fibrillation. Additionally, these rhythm monitors generally have limited storage capacity for storing monitoring data used to determine the extent of atrial fibrillation.

Atrial fibrillation is the most common disturbance of the heart rhythm requiring treatment. Epidemiologic data estimates that 2.2 million individuals suffer from atrial fibrillation in the United States. The incidence of AF increases with age. The prevalence of atrial fibrillation is approximately 2-3% in patients older than 40 years of age and 6% in those individuals over 65 years and 9% in individuals over 80 years old. Feinberg W M, Blackshear J L, Laupacis A, et al. *Prevalence, Age Distribution, and Gender of Patients With Atrial Fibrillation,* 155 Arch Intern Med. 469 (1995). As the US population ages, atrial fibrillation will become more prevalent. It is estimated that over 5 million Americans will suffer from atrial fibrillation by the year 2050. Go A S, Hylek E M, Phillips K A et al., *Prevalence of Diagnosed Atrial Fibrillation in Adults: National Implications for Rhythm Management and Stroke Prevention: the Anticoagulation and Risk Factors in Atrial Fibrillation (ATRIA) Study,* 285 JAMA, 2370 (2001). Atrial fibrillation is associated with a doubling of mortality rate of people afflicted with atrial fibrillation compared to people who are not, and an increased risk of stroke of about 5% per year. Fuster V, Ryden L E, Asinger R W, et al., *ACC/AHA/ESC Guidelines for the Management of Patients With Atrial Fibrillation,* 22 Eur. Heart J. 1852 (October 2001).

Atrial fibrillation can be either symptomatic or asymptomatic, and can be paroxysmal or persistent. Symptomatic atrial fibrillation is a medical condition wherein symptoms associated with atrial fibrillation are readily detectable by experts in the field. Atrial fibrillation is usually diagnosed when a patient reveals symptoms or complications associated with atrial fibrillation, such as congestive heart failure or stroke. Atrial fibrillation may also be diagnosed incidentally during a routine medical evaluation. Asymptomatic atrial fibrillation is a medical condition wherein symptoms normally associated with atrial fibrillation are either absent or are not readily detectable by experts in the field. Paroxysmal atrial fibrillation comprises occasional attacks of the atrial fibrillation condition on the patient. Persistent atrial fibrillation is a continuous existence of the atrial fibrillation condition. Patients with asymptomatic paroxysmal atrial fibrillation may be exposed to the risk of devastating consequences of atrial fibrillation such as stroke, congestive heart failure, or tachycardia mediated cardiomyopathy, for years before a definitive diagnosis of atrial fibrillation can be made. Current standard techniques and devices for detecting atrial fibrillation include a resting electrocardiogram, which records about 15 seconds of cardiac activity, a Holter monitor, which records 24-48 hours of cardiac activity during routine daily activities, and an event monitor, which only records cardiac activity when the patient activates the monitor because the patient has detected symptoms associated with atrial fibrillation. These diagnostic methods and tools have significant limitations in diagnosing atrial fibrillation and assessing the efficacy of treatment of atrial fibrillation because of the limited recording time windows of these methods and tools.

The prevalence of asymptomatic atrial fibrillation is difficult to assess, but is clearly underrepresented in the figures quoted above. Pharmacologic treatment of atrial fibrillation may convert patients with symptomatic atrial fibrillation into patients with asymptomatic atrial fibrillation. In a retrospective study of four studies comparing Azimilide drug to placebo where, in the absence of symptoms, routine trans-telephonic electrocardiograms were recorded for 30 seconds every two weeks, asymptomatic atrial fibrillation was present in 17% of the patients. Page R L, Tilsch B S, Connolly S J, et al., *Asymptomatic or "Silent Atrial Fibrillation: Frequency in Untreated Patients and Patients Receiving Azimilide,* 107 Circulation 1141 (2003). In another study of 110 patients with permanently implanted pacemakers who had a history of atrial fibrillation, atrial fibrillation was diagnosed in 46% of the patients using electrocardiogram ("EKG") recording and in 88% of the patients using stored electrograms recorded by the implanted pacemaker. Israel C W, Grönfefeld G, Ehrlich J R, et al., *Long-Term Risk of Recurrent Atrial Fibrillation as Documented by an Implantable Monitoring Device,* 43 J Am Coll Cardiol 47 (2004). Review of data stored in implanted devices, such as pacemakers, revealed that 38% of atrial fibrillation recurrences lasting greater than 48 hours were completely asymptomatic. Finally, using data obtained from ambulatory monitors used on patients with paroxysmal atrial fibrillation over a 24-hour period, studies show a high frequency of occurrence of asymptomatic atrial fibrillation among patients treated with propranolol or propafenone drugs. Wolk R, Kulakowki P, Karczmarewicz S, et al., *The Incidence of Asymptomatic Paroxysmal Atrial Fibrillation in Patients Treated With Propranolol or Propafenone,* 54 Int J Cardiol 207-(1996). In the above-mentioned study, 22% of the patients on propranolol and 27% of the patients on propafenone were diagnosed with atrial fibrillation without symptoms. There is also evidence that previously undetected atrial fibrillation is associated with stroke. About 4% of patients with stroke admitted to a medical facility also had newly diagnosed atrial fibrillation which was thought to be a precipitating cause of the stroke. Lin H J, Wolf P A, Benjamin E J, Belanger A J, D'Agostino R B, *Newly Diagnosed Atrial Fibrillation and Acute Stroke,* 26 The Framingham Study 1527 (1995).

Under-detection and under-recognition of atrial fibrillation in patients may have significant clinical consequences. A first consequence includes clinical exposure of patients to a significant risk of cardioembolic stroke before detection of the arrhythmia and initiation of appropriate stroke prevention measures. A second consequence includes difficulty of assessment of the efficacy of rhythm control intervention. Physicians caring for such patients may erroneously conclude that atrial fibrillation is no longer present and inappropriately discontinue anticoagulation treatments which may lead to a devastating cardioembolic stroke. Consequently, once diagnosed with atrial fibrillation, many patients may be committed to life-long anticoagulation by the physician to avoid the latter issues. A third consequence includes overestimation of successful maintenance of sinus rhythm. Clinical studies evaluating the efficacy of various rhythm control strategies may overestimate the successful maintenance of sinus rhythm as many of these studies report symptomatic atrial fibrillation as an endpoint. An accurate long term monitoring device would enhance the diagnostic yield of capturing asymptomatic paroxysmal atrial fibrillation, potentially allowing the safe withdrawal of anticoagulation treatments in patients treated successfully with antiarrhythmic agents, identifying the patients at risk who are currently not diagnosed as having atrial fibrillation, and providing a more precise measure of the efficacy of pharmacologic and nonpharmacologic rhythm control strategies.

Detection of atrial fibrillation, automatically or manually, based on statistical data, requires the use of thresholds defined with respect to sensitivity and specificity. The thresholds used define the point beyond which a set of data indicate existence of atrial fibrillation. Sensitivity and specificity are defined as follows. In a dichotomous experiment, a given event, e, falls into one of two sets, such as a set of positive events, P, and a set of negative events, N. The set P includes events p and the set N includes events n. A detection test may be performed to determine that the given event e belongs to the set P or to the set N in a dichotomous experiment. Sensitivity is a measure of how well the detection test can correctly identify the given event e of the set P as belonging to the set P. Such events e1 that are correctly identified as belonging to the set P are known as true positives ("TP"). Such events e that are misidentified as belonging to the set N are known as false negatives ("FN"). Sensitivity is defined as the ratio of the number of true positive events detected correctly by the test to the total number of actual positive events p. The total number of actual positive events is equal to the sum of the TP and FN. That is, sensitivity=TP/(TP+FN). A low sensitivity detection test will misidentify more positive events as belonging to the set N than a high sensitivity detection test. Specificity is the dual of sensitivity and is a measure of how well the detection test can correctly identify the given event e of the set N as belonging to the set N. Such events e that are correctly identified as belonging to the set N are known as true negatives ("TN"). Such events e that are misidentified as belonging to the set P are known as false positives ("FP"). Specificity is defined as the ratio of the number of true negative events detected correctly by the test to the total number of actual negative events n. The total number of actual negative events is equal to the sum of the TN and FP. That is, specificity=TN/(TN+FP). A low specificity detection test will misidentify more negative events as belonging to the set P than a high specificity detection test.

A number of techniques have been used for the automated detection of atrial fibrillation from digitized electrocardiograms. One of the techniques used includes the use of intracardiac recordings obtained from implanted devices showing a sensitivity of close to 100% and a specificity of greater than 99%. Swerdlow C D, Schsls W, Dijkman B, Jung W, Sheth N V, Olson W H, Gunderson B D, *Detection of A trial Fibrillation and Flutter by a Dual-Chamber Implantable Cardioverter-Defibrillator,* 101 Circulation 878 (2000). A method for analysis of the surface monitor leads using a wavelet transform achieved a sensitivity of 96% and specificity of 93% in recordings from patients with paroxismal atrial fibrillation. Duverney D, Gaspoz J M, Pichot V, Roche F, Brion R, Antoniadis A, Barthelemy J C, *High Accuracy of Automatic Detection of Atrial Fibrillation Using Wavelet Transform of Heart Rate Intervals,* 25 Pacing Clin Electrophysiol 457 (2002). At least one group has proposed using wavelets for implantable/wearable monitoring devices. Ang N H., *Real-Time Electrocardiogram (ECG) Signal Processing for Atrial Fibrillation (AF) Detection,* Modeling Seminar—Archive (2003). A prominent characteristic of atrial fibrillation is heart rate variability. There have been attempts to use the variability of heart interbeat ("RR") intervals directly to identify atrial fibrillation, resulting in a sensitivity of 94% and specificity of 97% using a threshold based on the Kolmogorov-Smirnov test. Tateno K, Glass L, *Automatic Detection of Atrial Fibrillation Using the Coefficient of Variation and Density Histograms of Rr and Deltarr Intervals,* 39 Med Biol Eng Comput. 664 (2001). The Kolmogorov-Smirnov test (*Chakravart, Laha, and Roy,* 1967) is used to decide if a statistical sample belongs to a population with a specific probability distribution.

Long-term monitoring of cardiac activity is desirable for timely detection of atrial fibrillation, but the storage requirements can be prohibitive. To digitize a single channel EKG at 100 samples per second and 10-bit resolution, which constitute near minimum requirements for a high quality signal, for 90 days of continuous recording requires 927 mega bytes (million bytes, "MB") of storage. Although providing this amount of storage is possible, it is also costly. Advances in electronics allow the design of portable devices that can preprocess and classify the signals to avoid storage of normal rhythms and save the storage capacity for recording of abnormal rhythms indicating existence of atrial fibrillation. Selective storage of signals that potentially indicate atrial fibrillation as opposed to normal heart rhythm, effectively increases the storage capacity and prolongs the recording period. At least two such devices exist in the market. One such device has been developed by Instromedix (San Diego, Calif.), and is available in two versions. Each version can monitor the heart rhythm for up to 30 days, capturing a total of 10 minutes of potentially abnormal EKG. The device weighs about 4 ounces. The other device is based on satellite telephone technology, and transmits the suspect rhythms to a monitoring facility. Recently, another device was announced with a detection rate of 90% and a monitoring storage capacity equivalent to 60 minutes of recorded data. A device for home use which does "momentary" analysis of the electrocardiogram as the patient grasps handles on the device daily is disclosed in U.S. Pat. No. 6,701,183, issued to Lohman Mar. 2, 2004, entitled Long Term Atrial Fibrillation Monitor.

A device is desired for the long-term monitoring of atrial fibrillation that is inexpensive, non-invasive, highly accurate, and convenient for the patient. These requirements at least indicate that the monitoring device should be light and small. As such, a device is desired with low power requirements and with a significant amount of storage. The storage capacity may possibly be extended by using an algorithm for the elimination of EKG data that indicate very low-probability of atrial fibrillation. This algorithm should be small in size and simple in operation to reduce processing power needs and electrical power requirements. The existing algorithms based on wavelets appear to be overly complex for this type of application requiring a significant amount of processing and electrical power as well as storage capacity.

SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method and a system for long-term monitoring and detection of an arrhythmia, the method comprising determining a number of heart beat intervals; determining an instantaneous heart rate for each of the heart beat intervals; determining the variability of the instantaneous heart rates compared to a mean of the number of instantaneous heart rates; determining a non-linear value that represents the variability of the instantaneous heart rates; and detecting the arrhythmia by comparing the non-linear value with a predetermined threshold.

In one exemplary embodiment of the invention, the portable monitoring system comprises a portable power source; at least one electrode for collecting heart rhythm data from a patient; a monitoring circuit coupled to the power source and the at least one electrode, wherein the monitoring circuit analyzes segments of the collected heart rhythm data to detect an arrhythmia; and a memory coupled to the monitoring circuit, wherein the memory stores the analyzed segments of collected heart rhythm data if an arrhythmia is detected.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A is a pictorial diagram of the portable atrial fibrillation monitoring and detection device shown in FIG. 1A;

FIG. 2B is a pictorial diagram of the portable atrial fibrillation monitoring and detection device shown in FIG. 1B;

FIG. 4A is a block diagram of an exemplary embodiment of a circuit for monitoring and detection of atrial fibrillation, including a hardware-based QRS signal detector;

FIG. 4B is a block diagram of another exemplary embodiment of a circuit for monitoring and detection of atrial fibrillation;

FIG. 5 is a pictorial diagram of a signal representing heart rhythm;

FIG. 6 is a pictorial diagram of a signal representing a QRS portion of heart rhythm;

DETAILED DESCRIPTION OF THE PREFERRED EMBODIMENT

A system and a method for long-term monitoring and detecting atrial fibrillation are described. While the system and method are ideally suited for detecting atrial fibrillation, the system and method may also find use in other environments. Furthermore, while the system and method are described in portable configurations and environments, the system and method may also find use in fixed and static environments. Thus, it is to be understood that the present invention should not be construed as limited in application to the exemplary embodiments described herein, and such exemplary embodiments should not be construed as limiting.

Figure 1B:
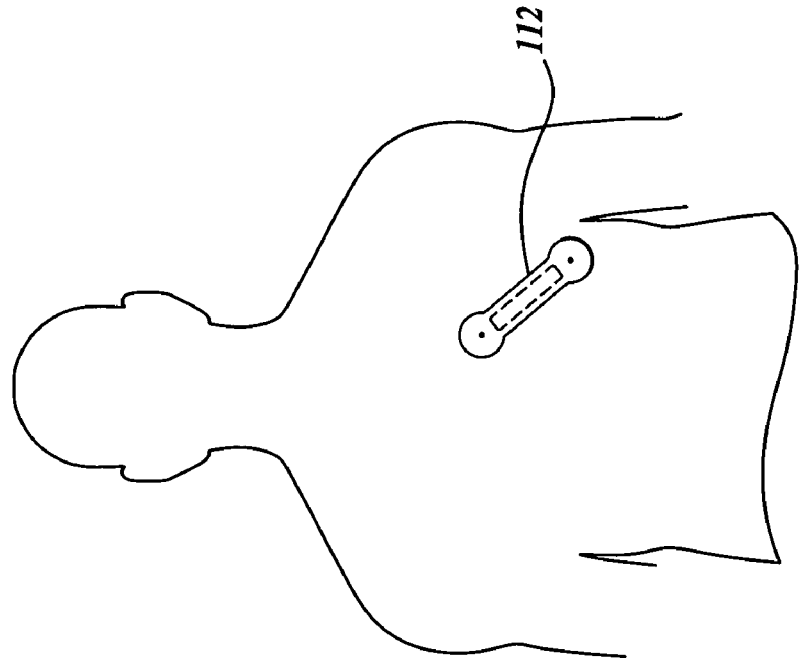
FIG. 1B is a pictorial diagram of another exemplary portable atrial fibrillation monitoring and detection device as applied to a patient.
Figure 1A:
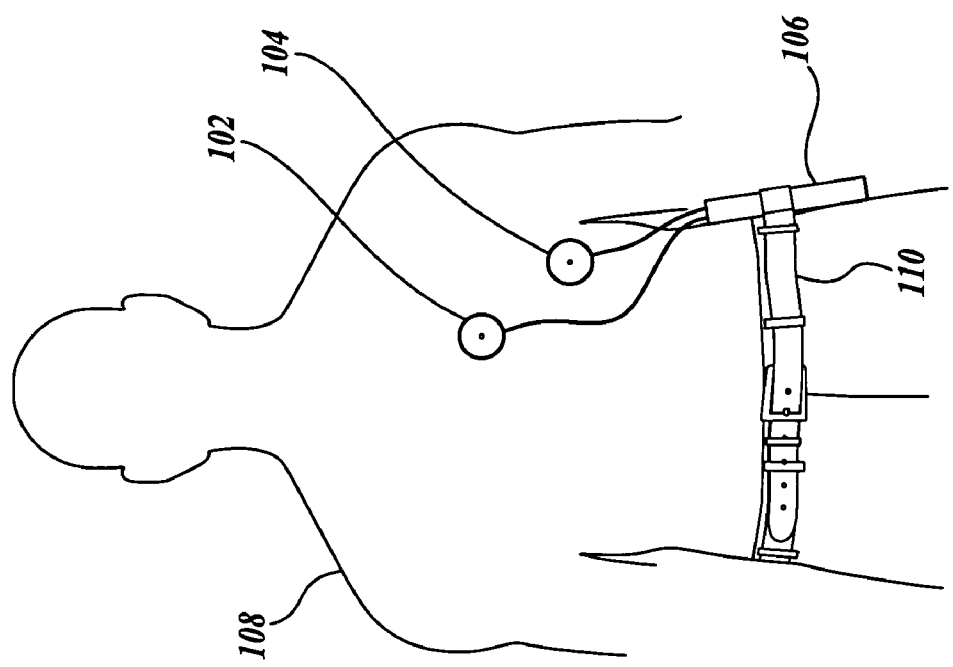
FIG. 1A is a pictorial diagram of an exemplary portable atrial fibrillation monitoring and detection device as applied to a patient.

FIG. 1A is a pictorial diagram showing an exemplary operating environment for a portable atrial fibrillation monitoring and detection device ("portable monitoring device"). This exemplary operating environment includes a light-weight, small, portable monitoring device 106 which can be used by a patient 108 daily or continuously for several months. The portable monitoring device 106 may be carried on a belt 110 or other harness. The portable monitoring device 106 includes at least two electrodes 102 and 104 which are attached to the body of the patient 108 for recording cardiac activity. In one exemplary embodiment, the electrodes 102 and 104 may be fixed to the portable monitoring device 106. In another exemplary embodiment, the electrodes 102 and 104 may be detachably connected to the portable monitoring device 106. The electrodes 102 and 104 may be attached to the body of the patient 108 using various means, including adhesive surfaces, rubber bands, or various kinds of straps and harnesses for holding the electrodes 102 and 104 in place. The electrodes 102 and 104 may also be attached to the body of the patient 108 by being attached to or implanted in the garment of the patient. The portable monitoring device 106 continuously collects data related to cardiac activity from the electrodes 102 and 104, and stores the collected data in the internal storage component of the portable monitoring device 106.

FIG. 1B is a pictorial diagram showing another exemplary operating environment for a portable atrial fibrillation monitoring and detection device. This exemplary operating environment includes a portable monitoring device and attached electrodes in one integrated monitoring device 112. In this exemplary operating environment, the integrated monitoring device 112 attaches directly to the body of the patient 108 without the need for the belt 110 or other harness for supporting the device. In this exemplary embodiment, the integrated monitoring device 112 is sufficiently thin and light-weight to securely attach to the body of the patient 108, for example, by means of adhesive surfaces, and to be worn under normal clothes without undue burden. The patient 108 wears the integrated monitoring device 112 for extended periods of time, removing and wearing the integrated monitoring device 112 as necessary for other activities, while noting the times of interruption of the recording operation.

FIG. 2A is a pictorial diagram showing an exemplary embodiment of a portable atrial fibrillation monitoring and detection device 202. Device configuration 200 includes the portable monitoring device 202, electrodes 214 and 216, and leads 212 coupling the electrodes 214 and 216 to the portable monitoring device 202. In one exemplary embodiment, the electrodes 214 and 216 may be fixed to the portable monitoring device 202. In another exemplary embodiment, the electrodes 214 and 216 may be detachably connected to the portable monitoring device 202. In one exemplary embodiment, the portable monitoring device 202 comprises at least one display 210, such as liquid crystal display ("LCD") panel, to show various information about the data and the status of the device. In another exemplary embodiment, the portable monitoring device 202 comprises an indicator 208, such as a light emitting diode ("LED"), to communicate information to the user of the device, for example, by blinking or by using different colors of light. The portable monitoring device 202 further comprises at least one input means 204, such as a button, to control the settings and the behavior of the portable monitoring device 202. In another exemplary embodiment, the portable monitoring device 202 comprises two such input means 204 and 206, one of which may be used by the patient and the other one by a technician during data retrieval or repairs. The portable monitoring device 202 further comprises at least one communication port 218 which is used to download and upload information to and from the portable monitoring device 202, respectively. The information communicated through port 218 includes data collected by, the device, device status, device configuration settings, and device software program update. In one exemplary embodiment, the portable monitoring device 202 further comprises internal circuitry (not shown in this figure) that include programmable devices, such as a microcontroller and a microprocessor, and internal software programs that are executed by the microcontrollers and microprocessors to cause the portable monitoring device 202 to collect data and perform other functions as discussed below. In another exemplary embodiment, the portable monitoring device 202 comprises internal circuitry (not shown in this figure) that include devices that operate independent of software for some aspects of the operation of the portable monitoring device 202, for example counting wave peaks and wave pattern detection. In one exemplary embodiment, the portable monitoring device has a weight of less than 3.5 ounces and a volume of less than eighty (80) cubic centimeters ("CC"). It will be appreciated by those skilled in the art that the shape and dimensions of the portable monitoring device 202 shown in FIG. 2A are for the purpose of illustration and discussion and should not be construed as a limit on the invention.

FIG. 2B is a pictorial diagram showing another exemplary embodiment of an integrated portable atrial fibrillation monitoring and detection device 250. In this exemplary embodiment, the integrated monitoring device 250 includes a processing component 256 built into the body of integrated monitoring device 250, and at least two integrated electrodes 252 and 254. In another exemplary embodiment, the integrated monitoring device 250 includes more than two integrated electrodes, taking the form of a star with multiple electrode arms extending from the body of the integrated monitoring device 250. In this exemplary embodiment, the integrated monitoring device 250 is sufficiently thin and light-weight to securely attach to the body of the patient, for example, by means of adhesive surfaces, and to be worn under normal clothes without undue burden. In one exemplary embodiment, the integrated monitoring device 250 further comprises internal circuitry (not shown in this figure) that include programmable devices, such as a microcontroller and a microprocessor, and internal software programs that are executed by the microcontrollers and microprocessors to cause the integrated monitoring device 250 to collect data and perform other functions as discussed below. In another exemplary embodiment, the integrated monitoring device 250 comprises internal circuitry (not shown in this figure) that include devices that operate independent of software for some aspects of the operation of the integrated monitoring device 250, for example counting wave peaks and wave pattern detection. It will be appreciated by those skilled in the art that the shape and dimensions of the integrated monitoring device 250 shown in FIG. 2B are for the purpose of illustration and discussion and should not be construed as a limit on the invention.

FIGS. 3A-D show several exemplary operating environments for downloading and uploading data from/to a portable atrial fibrillation monitoring and detection device. The portable monitoring device 302 shown in the above-mentioned drawings represents all embodiments of such monitoring device, including the portable monitoring device 202 and the integrated monitoring device 250 discussed above.

Figure 3C:
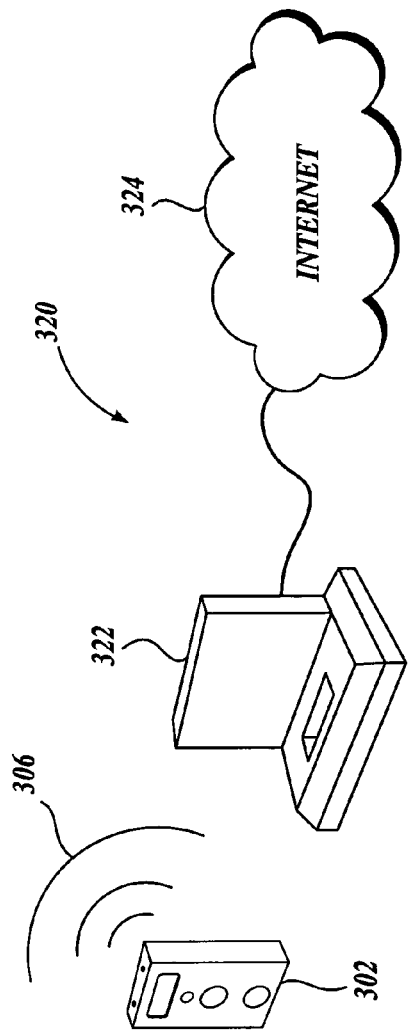
FIG. 3C is a pictorial diagram of another exemplary operating environment for downloading and uploading data from/to a portable atrial fibrillation monitoring and detection device.
Figure 3D:
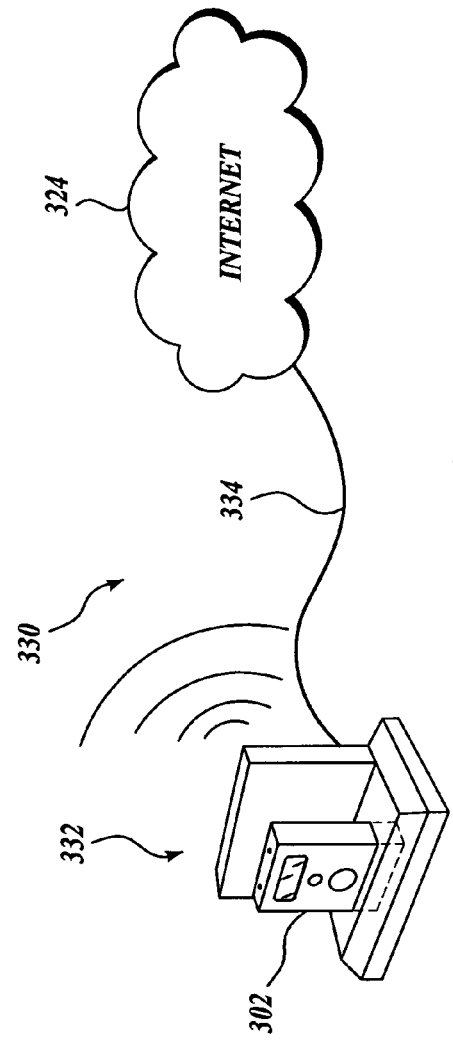
FIG. 3D is a pictorial diagram of another exemplary operating environment for downloading and uploading data from/to a portable atrial fibrillation monitoring and detection device.
Figure 3A:
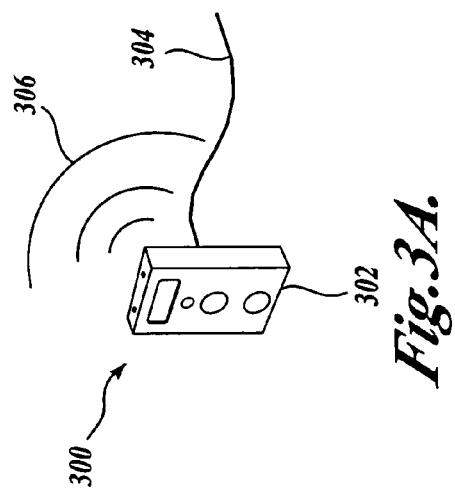
FIG. 3A is a pictorial diagram of an exemplary operating environment for downloading and uploading data from/to a portable atrial fibrillation monitoring and detection device.

FIG. 3A is a pictorial diagram showing an exemplary operating environment 300 for downloading and uploading data from/to a portable atrial fibrillation monitoring and detection device 302. In the operating environment 300, the portable monitoring device 302 communicates with a computer or other data processing equipment at a medical facility (not shown in this figure) where the collected data are used for processing and analysis and maintenance and setup operations are performed on the portable monitoring device 302. In one exemplary embodiment, the portable monitoring device 302 includes a wireless module which communicates data to a computer or other data processing equipment using electromagnetic waves 306. In one exemplary embodiment, the wireless module of the portable monitoring device 302 includes Bluetooth wireless interface. In another exemplary embodiment, the wireless module of the portable monitoring device 302 includes ZigBee wireless interface. In another exemplary embodiment, the portable monitoring device 302 uses a wired interface 304, for example, RS232 serial bus, universal serial bus ("USB"), and Firewire, to communicate data. The data communicated by the portable monitoring device 302 includes data collected by the device, device status, device configuration settings, and other similar information. The communication of data may be from or to the portable monitoring device 302. The portable monitoring device 302 may also receive information from outside, for example, from a technician or a computer, using the wireless module or the wired interface 304. Such information may include configuration settings and software program updates.

Figure 3B:
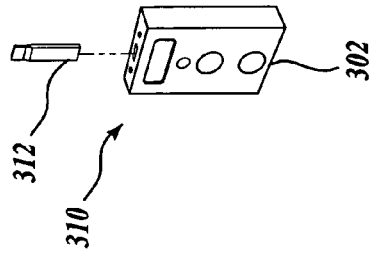
FIG. 3B is a pictorial diagram of another exemplary operating environment for downloading and uploading data from/to a portable atrial fibrillation monitoring and detection device.

FIG. 3B is a pictorial diagram showing another exemplary operating environment 310 for downloading and uploading data from/to a portable atrial fibrillation monitoring and detection device 302. In the operating environment 310, the portable monitoring device 302 communicates with a computer or other data processing equipment at a medical facility (not shown in this figure) where the collected data are used for processing and analysis and maintenance and setup operations are performed on the portable monitoring device 302. In one exemplary embodiment, the portable monitoring device 302 includes a removable memory module 312 which may be removed by a technician at a medical facility for retrieval of data collected by the portable monitoring device 302. In another exemplary embodiment, the memory module 312 is removed by the patient and mailed to the medical facility. Many types of memory devices are available that may be used as embodiments for the memory module 312. For example, in one embodiment, the memory module 312 includes a secure digital ("SD") memory card. In another exemplary embodiment, the memory module 312 includes a Personal Computer Memory Card International Association ("PCMCIA") flash type memory card. Yet in another exemplary embodiment, the memory module 312 includes a compact flash card. Still in another exemplary embodiment, the memory module 312 includes a Multimedia card ("MMC"). Still in another exemplary embodiment, the memory module 312 includes a memory stick. The information contained in the memory module 312 generally include the data collected by the portable monitoring device 302, but may optionally include other information, such as device status, device configuration settings, and device software program update. New software program updates for the portable monitoring device 302 may be included in the memory module 312.

FIG. 3C is a pictorial diagram showing another exemplary operating environment 320 for downloading and uploading data from/to a portable atrial fibrillation monitoring and detection device 302. In the operating environment 320, the portable monitoring device 302 communicates with a base station 322 at the patient's home or other remote location away from a medical facility where the collected data is processed and analyzed. The base station 322 may also be used for uploading software program updates, configuration settings, and other information to the portable monitoring device 302. In one exemplary embodiment, the portable monitoring device 302 includes a wireless module which communicates with base station 322 using electromagnetic waves 306. In one exemplary embodiment, the wireless module of the portable monitoring device 302 includes Bluetooth wireless interface. In another exemplary embodiment, the wireless module of the portable monitoring device 302 includes ZigBee wireless interface. In one exemplary embodiment, the base station 322 is connected to the Internet 324 using various methods of connection, such as a dialup connection, acoustic coupler, wired Ethernet connection, and WiFi. In another exemplary embodiment, the base station 322 is connected to the medical facility using a direct connection such as a dedicated network connection and direct dialup to a server used by the medical facility. The data from the portable monitoring device 302 is transferred to a medical facility where the data is processed and analyzed using the base station 322 and the Internet 324 or other connections, as discussed above.

FIG. 3D is a pictorial diagram showing another exemplary operating environment 330 for downloading and uploading data from/to a portable atrial fibrillation monitoring and detection device 302. In one embodiment, the portable monitoring device 302 is seated in a base station 332 whereby an electrical data interface is used to establish a connection between the portable monitoring device 302 and the base station 332. In one exemplary embodiment, the base station 322 is connected to the Internet 324 using various methods of connection, such as a dialup connection, acoustic coupler, wired Ethernet connection, and WiFi. In another exemplary embodiment, the base station 322 is connected to the medical facility using a direct connection such as a dedicated network connection and direct dialup to a server used by the medical facility. The data from the portable monitoring device 302 is transferred to a medical facility where the data is processed and analyzed using the base station 332 and the Internet 324 or other connections, as discussed above.

FIG. 4A is a block diagram showing an exemplary embodiment of a circuit 400 for monitoring and detection of atrial fibrillation, including a hardware-based QRS complex signal detector 416 ("QRS detector"). In one exemplary embodiment, the monitoring circuit 400 includes a preamplifier 402 for amplifying the analog electrocardiographic signals detected by electrodes and presented at input terminals 418 and 420. The output of the preamplifier 402 is input to microprocessor 408 and QRS detector 416. In one embodiment, the QRS detector 416 comprises a peak detector. In another embodiment, the QRS detector 416 comprises a peak detector with hysteresis. Yet in another embodiment, the QRS detector 416 comprises a signal correlator that matches an input signal to a reference signal (not shown in this figure). The microprocessor 408 is coupled with a data interface 412 via a data bus 414. The microprocessor 408 is further coupled with a data storage component 410 used for storing data collected by the microprocessor 408 from the preamplifier 402 and for storing software programs executed by the microprocessor 408. A power supply 404 supplies power to all electronic components using power bus 406. In one exemplary embodiment, the power supply 404 comprises a battery. In one exemplary embodiment, the electronic components used in the monitoring circuit 400 are off-the-shelf components. In another exemplary embodiment, the electronic components comprise application-specific integrated circuits ("ASIC") or other custom-made electronics. In one embodiment, the microprocessor is a high-integration component including an analog-to-digital ("A/D") converter and memory and data interfaces. The microprocessor and other electronic components are selected to have low power consumption. Low power consumption of electronic components enables the monitoring circuit 400 to operate continuously for extended periods of time on a limited power source, such as a battery. It will be appreciated by those skilled in the art that other electronic components not shown in FIG. 4A, such as LCD display, buttons, LED, and the like, may be coupled to the circuit 400.

The operation of the monitoring circuit 400 includes the pre-amplification of the analog electrocardiographic signals at input terminals 418 and 420 by the preamplifier 402. The amplified analog electrocardiographic signal at the output of preamplifier 402 is transmitted to the microprocessor 408 and QRS detector 416. The microprocessor 408 converts the analog electrocardiographic signal from the output of the preamplifier 402 to a digital electrocardiographic signal suitable for manipulation by a software program running on the microprocessor 408. In one embodiment, the software program running on the microprocessor 408 is stored in a designated section of the data storage component 410. In another embodiment, the software program running on the microprocessor 408 may be stored in a different memory component (not shown in this figure) that is distinct from the data storage component 410. Yet in another embodiment, the software program running on the microprocessor 408 may be stored in a memory component integrated with the microprocessor 408 on the same electronic chip. The microprocessor 408 receives an output signal of the QRS detector 416 when the QRS detector 416 detects a QRS complex signal which periodically appears as a segment of the electrocardiographic signal. The software program running on the microprocessor 408 analyzes the electrocardiographic signal digitized by the microprocessor 408 and the output signal received from the QRS detector 416 and classifies the digitized electrocardiographic signal as either atrial fibrillation or other cardiac rhythms using an algorithm 1000, described below. The QRS detector 416 reduces the computational load on the microprocessor 408 by detecting the QRS complex signal and notifying the microprocessor 408 by the output signal from the QRS detector 416. If the digitized electrocardiographic signal is classified as atrial fibrillation, then the digitized electrocardiographic signal is retained as digital electrocardiographic data in the data storage component 410. If the digitized electrocardiographic signal is classified as a cardiac rhythm other than atrial fibrillation, then the digitized electrocardiographic data is not retained in the data storage component 410. Thus, only the digitized electrocardiographic data representing atrial fibrillation is retained in the data storage component 410, saving memory space which would otherwise be used for storing all digitized electrocardiographic data. For example, using a method 1100 for detecting atrial fibrillation, discussed below, and the example given above for 90 days of continuous recording of a single channel EKG at 100 samples per second and 10 bits per resolution, requires about 46 MB of storage rather than 927 MB.

In one embodiment, the software program running on the microprocessor 408 compresses the digital electrocardiographic data before storing the digital electrocardiographic data in the data storage component 410. Such compression effectively increases the storage capacity of the data storage component 410. In one embodiment, the monitoring circuit 400 gives an indication to the user of the portable monitoring device 202, for example, the patient, that the electrocardiographic data retained in the data storage component 410 is ready for retrieval. In one embodiment, the indication to the user is produced when a predetermined amount of data has been retained in the data storage component 410. In another embodiment, the indication to the user is produced when a predetermined amount of time has elapsed. Those skilled in the art will appreciate that the indication to the user may be produced based on criteria other than those mentioned above. The user of the portable monitoring device 202 retrieves the electrocardiographic data retained in the data storage component 410 by one of the methods discussed above with respect to FIGS. 3A-D. The electrocardiographic data may be analyzed further by more advanced methods after retrieval.

FIG. 4B is a block diagram showing another exemplary embodiment of a circuit 450 for monitoring and detection of atrial fibrillation. The components and operation of the circuit 450 are substantially similar to the circuit 400 described above with respect to FIG. 4A, except for lacking the QRS detector 416 shown in FIG. 4A. The functions performed by the QRS detector 416 in circuit 400, are performed by a microprocessor 458 under software control. Therefore, the software program stored in a data storage component 460 is executed by the microprocessor 458 to cause the detection of an analog electrocardiographic signal, including a periodic QRS complex segment. The analog electrocardiographic signal is input at input terminals 468 and 470, amplified by a preamplifier 452, and transmitted to the microprocessor 458. As discussed above with respect to FIG. 4A, the microprocessor 458 digitizes the analog electrocardiographic signal which is used by the software program to detect the periodic QRS complex. As mentioned above, the operation of the circuit 450 is otherwise the same as the circuit 400 discussed above. As discussed above, it will be appreciated by those skilled in the art that other electronic components not shown in FIG. 4B, such as LCD display, buttons, LED, and the like, may be coupled to the circuit 450.

Figure 11:
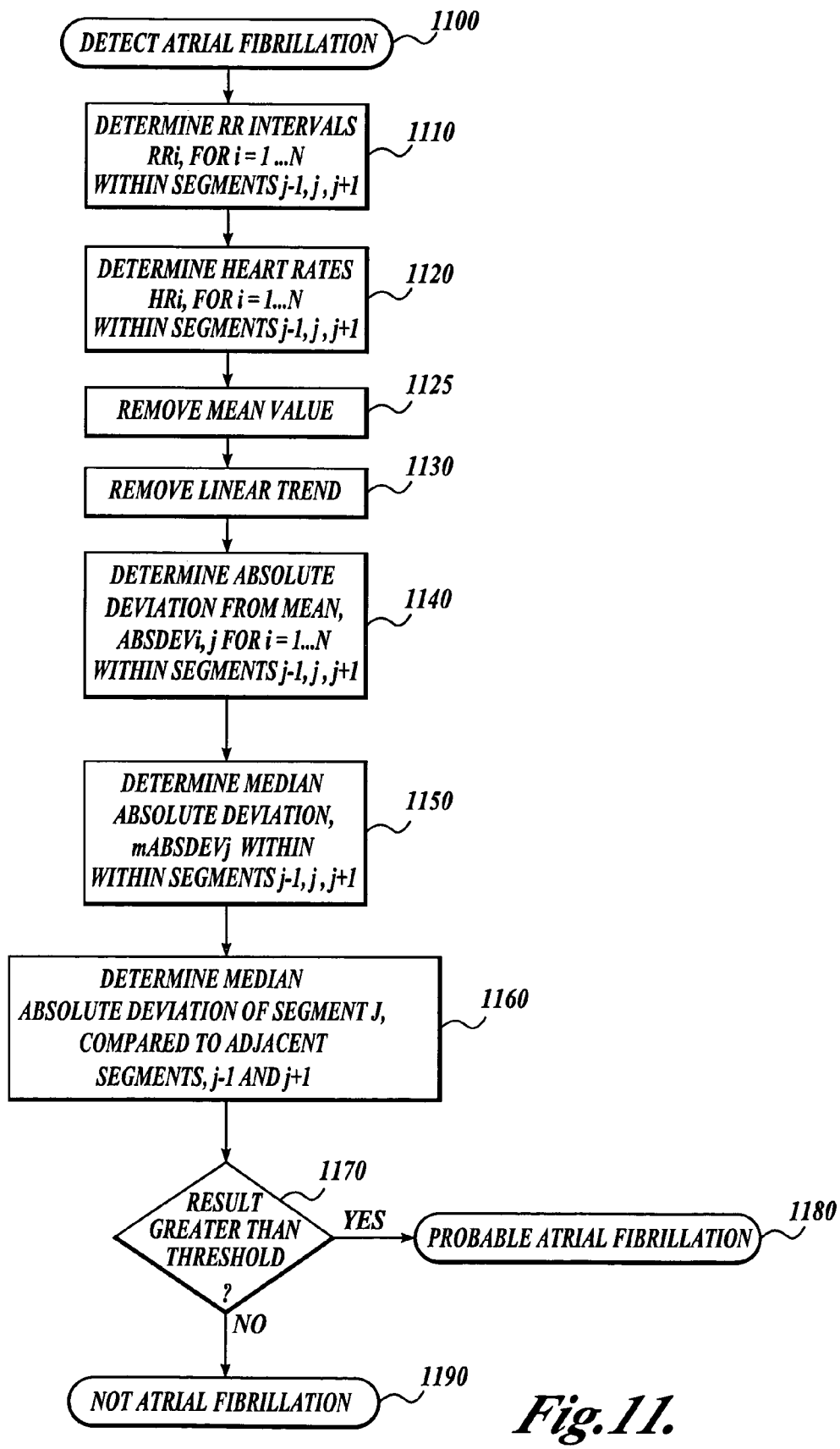
FIG. 11 is a flow diagram of an exemplary atrial fibrillation detection method.
Figure 12:
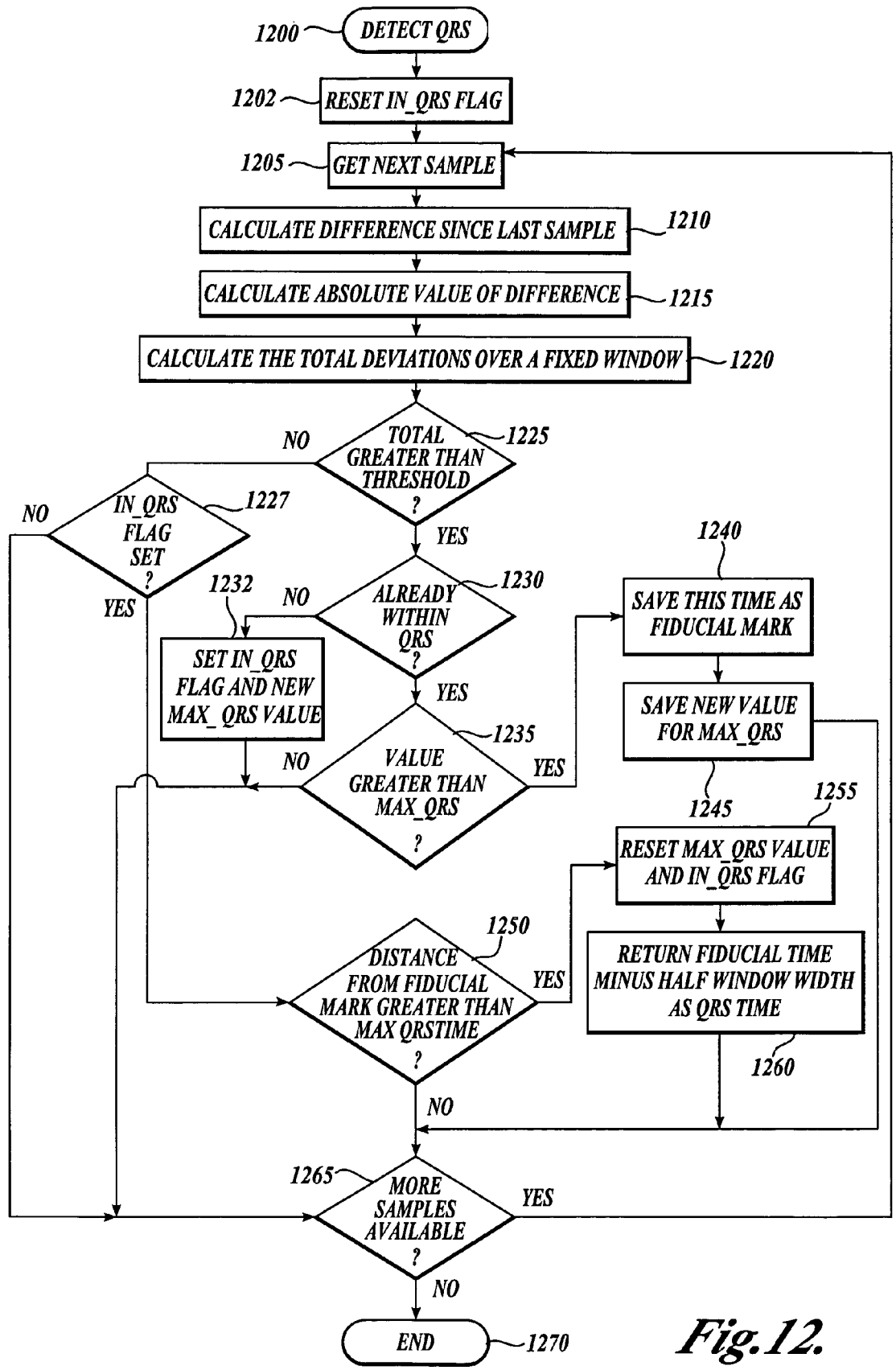
FIG. 12 is a flow diagram of an exemplary QRS detection method.

FIG. 5 is a pictorial diagram of a signal 500 representing heart rhythm. The heart rhythm 500 comprises a repeating pattern of several distinct segments, including a QRS complex 502. The QRS complex 502 comprises a peak 504. The time interval between two consecutive peaks 504 is the interbeat interval 506 ("RR interval"). The peak 504 is one of the QRS 502 features which can be used to detect a QRS complex 502. Instantaneous heart rate is the inverse of the RR interval 506, that is, instantaneous heart rate equals 1/RR, for each RR interval 506. Methods 1100 and 1200, discussed below in more detail with respect to FIGS. 11 and 12, are used to detect atrial fibrillation by analyzing an electrocardiogram with a high degree of accuracy. Methods 1100 and 1200 are based on the variability of RR interval 506 that is a characteristic of atrial fibrillation. Method 1100 uses the actual time of occurrence of the QRS complexes 502 to detect atrial fibrillation. The RR interval 506 (beat-to-beat) variation of heart rate is computed using the absolute value of the difference of each RR interval 506 heart rate from the local mean, which is the mean value for a selected number of RR intervals 506 used for the computation. Each RR interval 506 is used to compute the instantaneous heart rate for the RR interval 506. The sequence of these instantaneous heart rates for each R-R interval 506 is used for detecting atrial fibrillation. The heart rates obtained are not averaged over fixed time intervals, thus avoiding loss of variability data over the fixed time intervals.

FIG. 6 is a pictorial diagram of a signal 600 representing QRS portion 602 of heart rhythm. The QRS complex 602 comprises a wave valley section Q 608, a peak section R 610, and another valley section QS 614. As discussed above, the QRS complex appears periodically in heart rhythm. The time of appearance of each QRS complex 602 is used to detect the variability of heart rhythm and atrial fibrillation.

Figure 7:
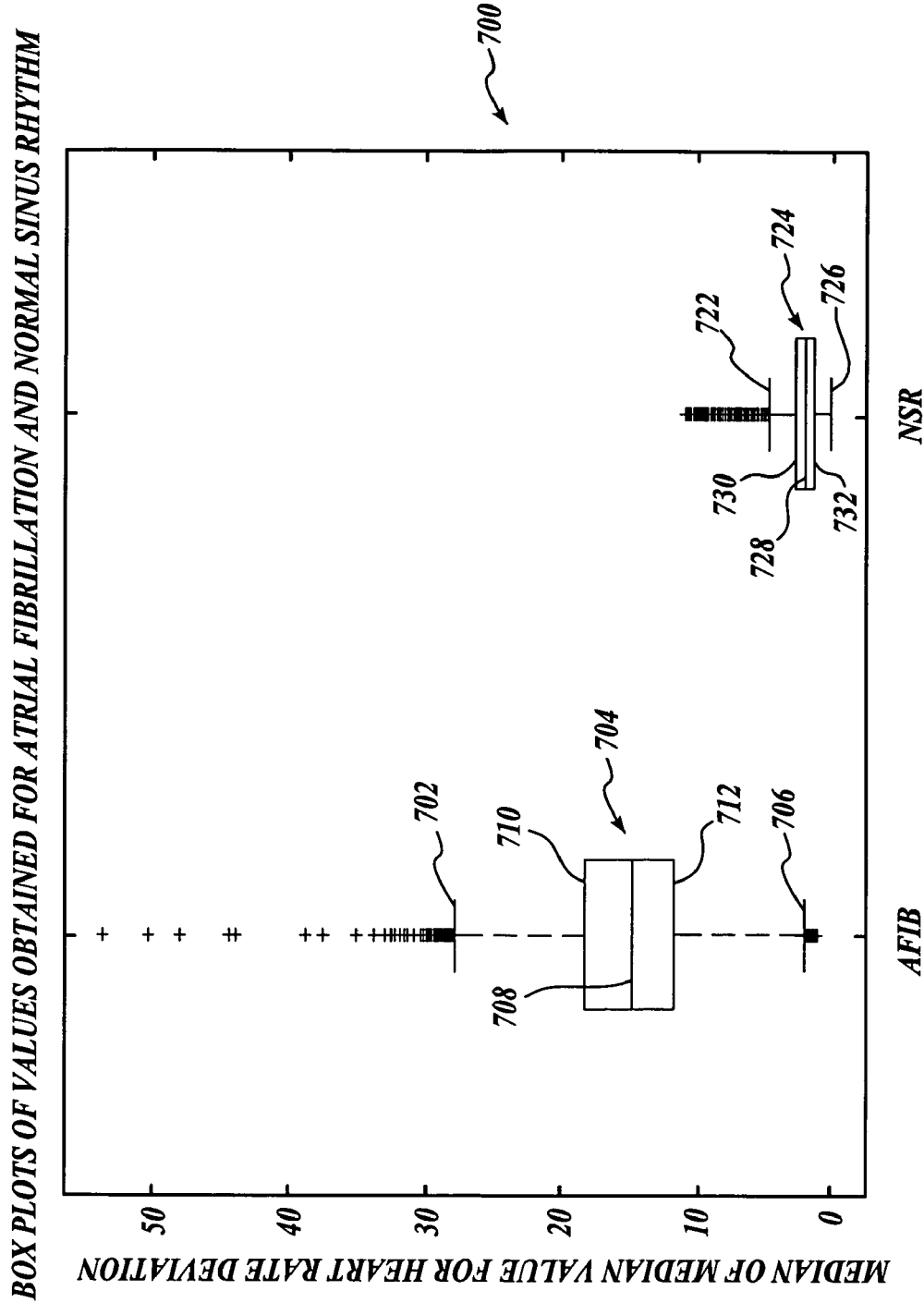
FIG. 7 is an exemplary box plot graph of values obtained for atrial fibrillation and normal heart rhythm.

FIG. 7 is a pictorial diagram showing exemplary box plots 700 of values obtained for atrial fibrillation 704 and normal heart rhythm 724. The box plots 704 and 724 are constructed based on a local deviation of the heart rate. The local deviation is closely related to variance, indicating the variability of heart rate. Bassingthwaighte J B, Raymond G M, *Evaluation of the Dispersional Analysis Method for Fractal Time Series*, 23 Ann Biomed Eng. 491 (1995). The vertical axis of box plots 700 is the median of median values for heart rate deviation. Box plot 704 comprises a mean value 708, an upper edge 710 indicating the 75th percentile located above the mean 708, a lower edge 712 indicating the 25th percentile located below the mean 708, an upper line 702 indicating 1.5 interquartile (interquartile range is a measure of spread or dispersion and is the difference between the 75th percentile and the 25th percentile) above the mean 708, and a lower line 706 indicating 1.5 interquartile below the mean 708. Similarly, box plot 724 comprises a mean value 728, an upper edge 730 indicating 75th percentile located above the mean 728, a lower edge 732 indicating 25th percentile located below the mean 708, an upper line 722 indicating 1.5 interquartile above the mean 728, and a lower line 726 indicating 1.5 interquartile below the mean 728. Based on the variability of heart rate indicated by box plots 704 and 724, significant discrimination between atrial fibrillation and normal sinus rhythm exists, which discrimination is detectable by the method 1100, discussed below, using the median of median values for heart rate deviation. A median of a number of statistical samples is significant because the median is a non-linear average value representing the statistical samples and is defined as the middle value of a sorted list of the statistical samples. It is non-linear with respect to the values of the statistical samples because the value of the median does not change with value of each statistical sample, in contrast to a mean value of the same samples. The mean value changes linearly with the changes in the values of the statistical samples because the mean is equal to the sum of the values of all the statistical samples divided by the number of the statistical samples. Thus, the median value is not sensitive to and does not change as a result of sample values at the extreme ends of a statistical population.

Figure 8:
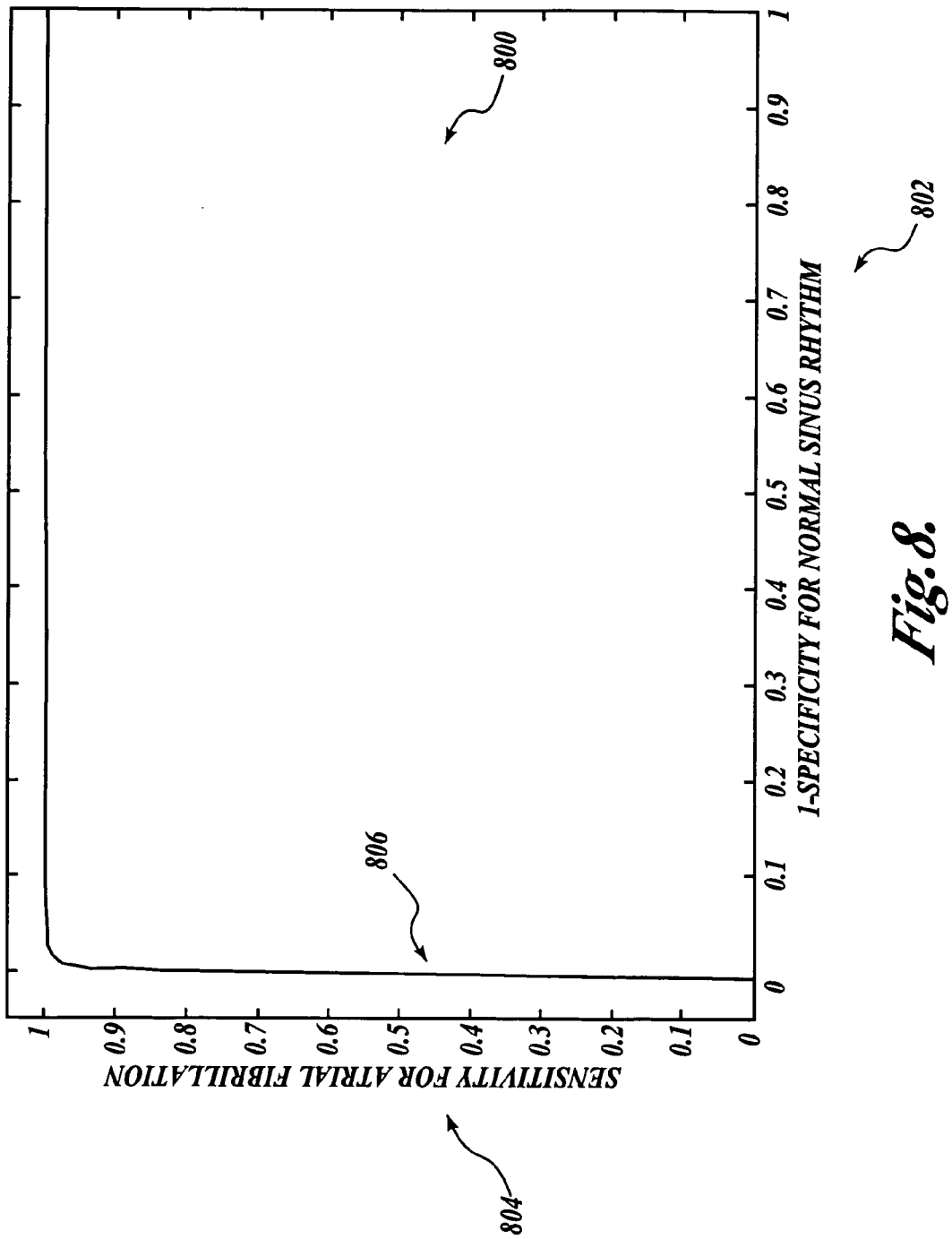
FIG. 8 is a pictorial diagram showing an exemplary plot graph of values for Sensitivity versus 1—Specificity with a variable threshold for detection of atrial fibrillation.

FIG. 8 is a pictorial diagram showing an exemplary plot 800 of values for Sensitivity versus 1—Specificity with a variable threshold for detection of atrial fibrillation. The plot 800 comprises a receiver operator curve ("ROC") 806. Each point on the ROC 806 is obtained by plotting sensitivity value 804 versus one minus specificity (1—specificity) value 802. Each sensitivity value 804 and corresponding specificity value are calculated based on a different threshold value (not shown in this figure) comprising a median of median values for heart rate deviation. A median of median values for heart rate deviation, discussed above with respect to FIG. 7, above a given threshold value is considered to indicate atrial fibrillation subject to error rates defined by sensitivity and specificity values. More specifically, errors in detection of atrial fibrillation are classified as false positives ("FP") and false negatives ("FN"), as discussed above in the background section. Threshold values are selected such that sensitivity and specificity values are maximized. The median values are also affected by the number of RR intervals 506 used to calculate the variability of heart rate, which is more fully discussed below with respect to FIG. 11. The bend in the ROC 806 is the point which corresponds to the threshold that results in minimal error, that is, maximal sensitivity and specificity.

Figure 9:
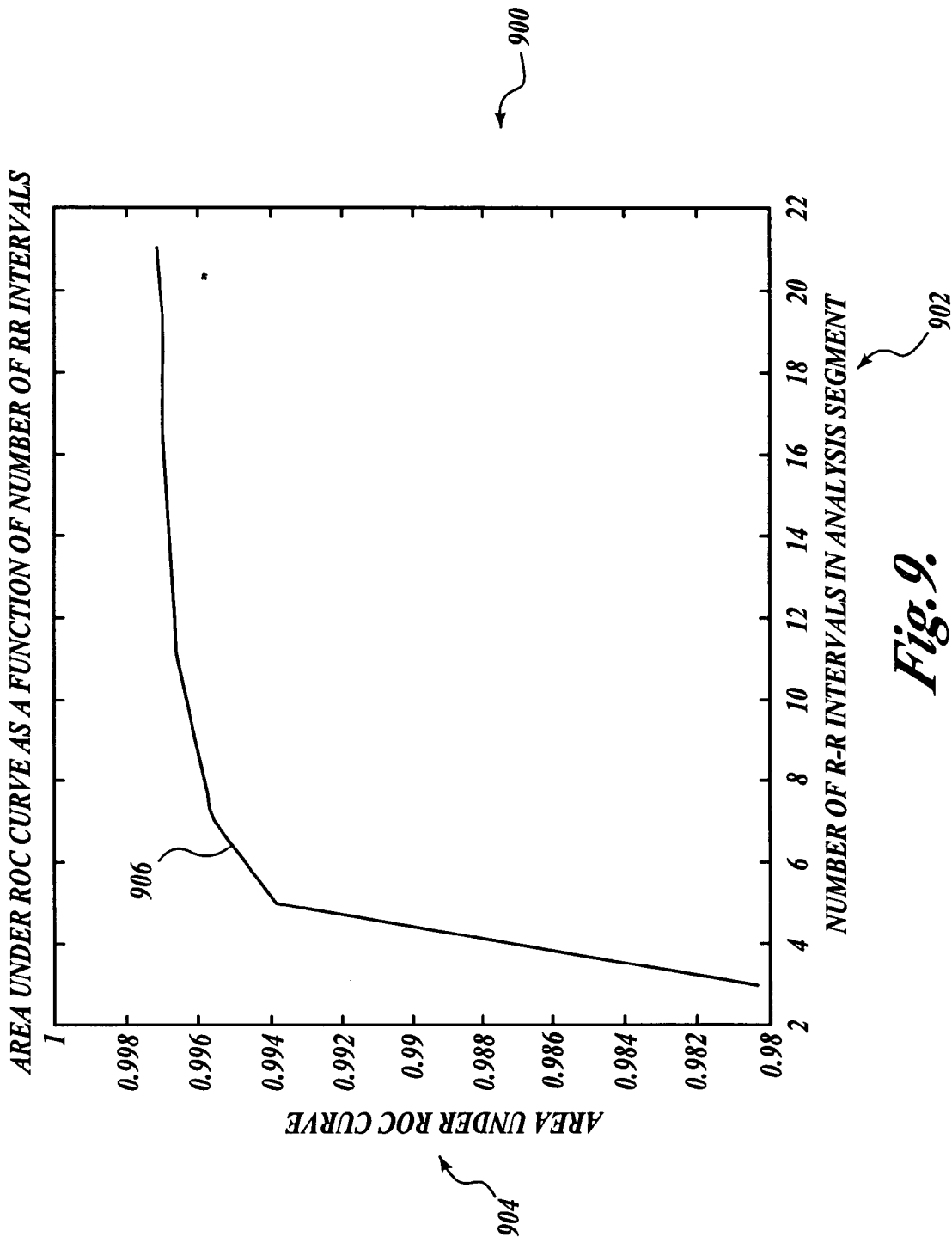
FIG. 9 is an exemplary plot graph of a number of RR intervals versus area under a Receiver Operator Curve ("ROC")

FIG. 9 is a pictorial diagram showing an exemplary plot 900 of number of RR intervals 902 versus area under the ROC 904. The plot 900 comprises an area under ROC curve 906 obtained by plotting area under each ROC 806, as plotted in FIG. 8, versus number of RR intervals 902 used in calculating median of median values for heart rate deviation. Sensitivity and specificity increase when the number of RR intervals 902 increases, resulting in a larger area under the ROC 904, which has a maximum value of 1. The bend in the area under ROC curve 906 corresponds to the number of RR intervals 902 at which the area under ROC curve 906 is near maximum. Use of a larger number of RR intervals 902 only marginally increases the area under ROC curve 906 while greatly increasing the computational load on the portable monitoring device 202. Therefore, by plotting the area under ROC curve 906, a near optimal number of RR intervals 902 may be obtained, minimizing the number of RR intervals 902 to be used in calculations while maximizing the sensitivity and specificity defined by the corresponding ROC 806. For example, if 19 RR intervals 902 are used for computation, a threshold may be chosen that provides a sensitivity value of 98.0% and specificity value of 98.7%. The above-mentioned sensitivity and specificity values are close to those resulting from using 7 RR intervals 902 (98.0% and 97.2%, respectively), but the cost of computation and storage with 19 RR intervals 902 is greater than with 7 RR intervals 902.

Figure 10:
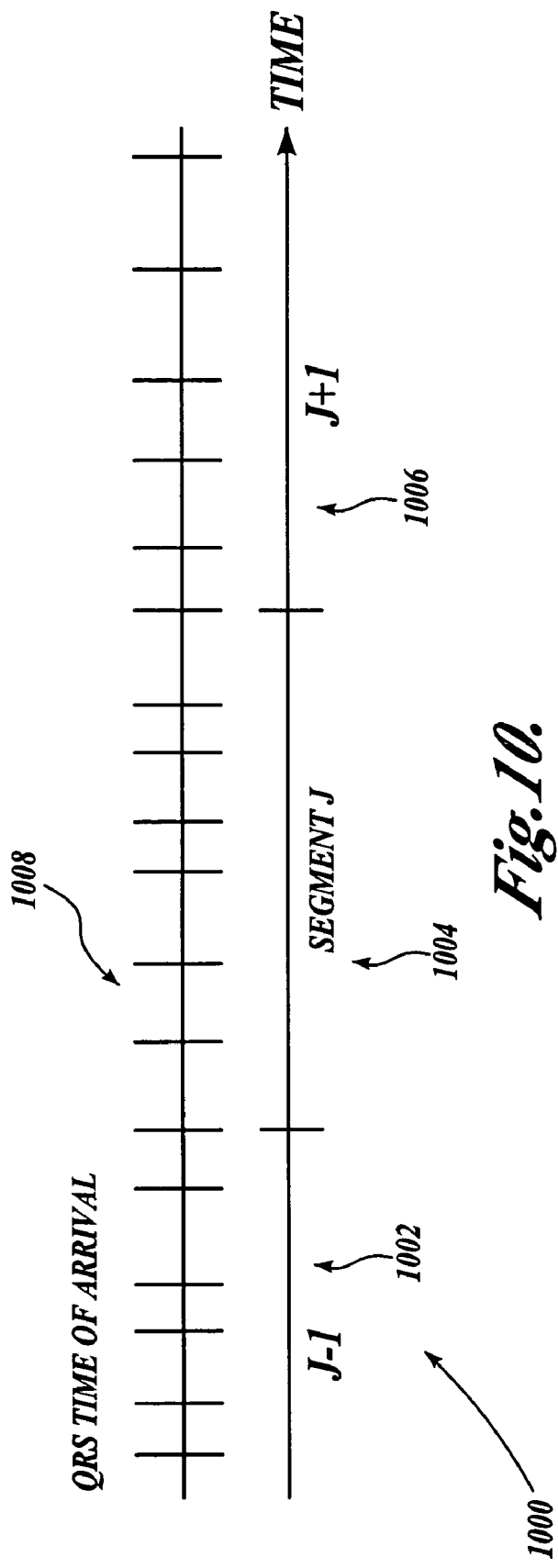
FIG. 10 is an exemplary time line of RR intervals.

FIG. 10 is a pictorial diagram showing an exemplary set of three segments of RR intervals 1008. The three segments include segment J−1 1002, segment J 1004, and segment J+1 1006. Each of the segments J−1 1002, J 1004, and J+1 1006 is further subdivided into an equal number of RR intervals 902. Each RR interval is measured based on the actual arrival time of each QRS complex 502, as shown in FIG. 5. The above-mentioned segments are used in method 1100 discussed below.

FIG. 11 is a flow diagram of an exemplary atrial fibrillation detection method 1100. The method 1100 measures the variability of heart rate by calculating the instantaneous heart rate based on actual arrival times of QRS signals 502. The method 1100 further compares a non-linear value representing the variability of heart rate to a threshold. The method 1100 determines the existence of atrial fibrillation based on the result of the comparison. The flow diagram proceeds to block 1110 where the size of each RR interval 902 is determined within each of a number of segments, for example, the three segments J−1 1002, J 1004, and J+1 1006 shown in FIG. 10. It will be appreciated by those skilled in the art that any number of segments may be used for this calculation and the choice of three segments is for the purpose of illustration only and is not to be construed as a limitation on the invention. The flow diagram proceeds to block 1120 where instantaneous heart rates corresponding to each RR interval 902 are determined within each of the segments J−1 1002, J 1004, and J+1 1006 separately. In block 1125 the mean values of each of the J−1 1002, J 1004, and J+1 1006 are removed. In block 1130 the linear trend is removed to improve estimation of variability of instantaneous heart rate. In block 1140 the absolute deviation from mean is determined for each RR interval 902 within each of the segments J−1 1002, J 1004, and J+1 1006. In block 1150 the median of absolute deviation from mean for each RR interval 902 is determined. In block 1160 the median of medians of all three segments J−1 1002, J 1004, and J+1 1006 is obtained. In block 1170 the median of medians of all three segments J−1 1002, J 1004, and J+1 1006 is compared with a chosen threshold value. If the median of medians of all three segments J−1 1002, J 1004, and J+1 1006 is greater than the chosen threshold, then existence of atrial fibrillation is probable. Otherwise, atrial fibrillation is unlikely to exist during the three segments J−1 1002, J 1004, and J+1 1006.

FIG. 12 is a flow diagram of an exemplary QRS detection method 1200. As discussed above with respect to FIG. 4B, method 1200 may be used by a software program executed by the microprocessor 458 to detect a QRS complex 602. The method 1200 detects the QRS complex 602 by summing up the absolute value of the amplitudes of the signal samples that fall within a QRS complex 602 time window and comparing the sum with a threshold. More specifically, In block 1202, an IN_QRS flag is reset to indicate that the currently the signal being evaluated is outside of the QRS time window. In block 1205 a next signal sample is obtained for detection of the QRS complex 602. In block 1210, an amplitude difference between the next signal sample and the immediate previous signal sample is calculated. In block 1215, an absolute value of the amplitude difference between the next and the immediate previous signal samples is calculated. In block 1220, the total of the absolute values of amplitude differences over a predetermined time window is calculated. In block 1225, the total of the absolute values of amplitude differences is compared with a threshold. If the total of the absolute values of amplitude differences is greater than the threshold, the flow diagram proceeds to block 1230 where it is determined whether the time of the next signal sample is within the time window of the QRS complex 602. Otherwise, the flow diagram proceeds to block 1250. Back in block 1230, if the time of the next signal sample is within the QRS complex 602, the flow diagram proceeds to block 1235 where it is determined whether the total of the absolute values of amplitude differences of the next signal sample is greater than a current maximum QRS amplitude value, MAX_QRS. If the total of the absolute values of amplitude differences is greater than MAX_QRS, the flow diagram proceeds to block 1240 where the time of the next signal sample is marked as a fiducial point. The flow diagram proceeds to block 1245 where the value of the maximum QRS is updated and set to the total of the absolute values of amplitude differences. The flow diagram proceeds to block 1265 where it is determined if more sample signals available. If more sample signals available, the flow diagram proceeds back to step 1205 to get the next signal sample. Otherwise, the flow diagram terminates at block 1270.

Back in block 1225, if the total of the absolute values of amplitude differences is not greater than the variation threshold, the flow diagram proceeds to block 1227 where the state of the IN_QRS flag is determined. If the IN_QRS flag is set, the flow diagram proceeds to block 1250. Otherwise, the flow diagram continues to block 1265. In block 1250, the flow determines whether the time distance from the fiducial mark is greater than a maximum QRS time value, MAX_QRSTIME. MAX_QRSTIME indicates the maximum time span that a QRS complex 602 may have. If the time distance from the fiducial mark is greater than the MAX_QRSTIME, the flow diagram proceeds to block 1255 where the MAX_QRS value and IN_QRS flag are reset. The flow diagram proceeds to block 1260, where the difference between the fiducial time and half the predetermined time window is provided by the method 1200 as the time of the QRS signal. Back in block 1230, if the time of the next signal is not within the QRS complex 602, the flow diagram proceeds to block 1232 where an IN_QRS flag is set to indicate the start of a new QRS complex 602, and a value is set for the maximum QRS. The flow diagram proceeds to block 1265 and continues as discussed above.

The methods and systems described above allow identification of patients at risk due to otherwise undetected atrial fibrillation. For example, studies may be performed to assess the risk as a function of the amount and duration of atrial fibrillation, in the patients known to have paroxismal atrial fibrillation.

While the preferred embodiment of the invention has been illustrated and described, it will be appreciated that various changes can be made therein without departing from the spirit and scope of the invention. For example, while the methods and systems described above are directed towards the detection of atrial fibrillation, other infrequent but clinically significant rhythm disturbances, such as ventricular tachycardia or intermittent high-grade atrioventricular block, may be detected by substantially similar methods and systems.

The embodiments of the invention in which an exclusive property or privilege is claimed are defined as follows:

1. A method for detection of an arrhythmia, the method comprising:
    monitoring the electrical with a monitoring device to produce data representing the heart rhythm;
    selecting a number of sequential segments of the data, each segment comprising a fixed number of heart beat intervals;
    determining a duration of each heart beat interval in each of the selected number of segments;
    calculating an instantaneous heart rate for each heart beat interval in each of the selected number of segments;
    calculating a mean instantaneous heart rate for the fixed number of heart beat intervals within each of the selected number of segments;
    within each of the selected number of segments, calculating an absolute deviation from the mean instantaneous heart rate for each of the fixed number of heart beat intervals within the segment;
    within each of the selected number of segments, selecting a median value of the absolute deviations from the mean instantaneous heart rate;
    among the selected number of segments, selecting a median of the median values of each of the segments to be a test value; and
    identifying the arrhythmia by comparing the test value with a predetermined threshold.

2. The method of claim 1 wherein the arrhythmia is atrial fibrillation.

3. The method of claim 1 wherein the selected number of segments is at least three.

4. The method of claim 1 wherein the predetermined threshold is dynamically determined prior to the comparison.

5. The method of claim 1 wherein the number of heart beat intervals in each segment is at least seven.

6. The method of claim 1, further comprising the step of: within each of the selected number of segments, removing a linear trend from the instantaneous heart rates prior to calculating an absolute deviation from the mean instantaneous heart rate for each of the fixed number of heart beat intervals within the segment.

7. A method for detection of an arrhythmia, the method comprising:
    monitoring the electrical activity of a heart with a monitoring device to generate a signal representing the beating of the heart;
    determining a first number of sequential segments, each of the segments including a second number of heart beat intervals;
    determining arrival time of a QRS complex portion of the signal representing each heart beat;
    using the arrival times of the QRS complex portions to determine an instantaneous heart rate for each of the heart beat intervals;
    determining an absolute deviation of the instantaneous heart rates compared to a mean of the instantaneous heart rates for each of the first number of segments;
    applying a non-linear function to the absolute deviations of the instantaneous heart rates to determine a value for each segment that represents the variability of the instantaneous heart rates in that segment;
    wherein the step of applying a non-linear function to the absolute deviations of the instantaneous heart rates comprises:
    determining a mean value of the instantaneous heart rates within each segment;
    determining an absolute deviation of each instantaneous heart rate from the mean value of each segment;
    determining a median value of the absolute deviation of each instantaneous heart rate from the mean value for each of the segments; and
    determining a median of the median values of each of the segments selecting the median value of the values over the first number of segments to be a test value for detecting arrhythmia; and
    detecting arrhythmia by comparing the test value with a predetermined threshold.

8. The method of claim 7 wherein the arrhythmia is atrial fibrillation.

9. The method of claim 7 wherein the number of segments is at least three.

10. The method of claim 7 wherein the predetermined threshold is dynamically determined prior to the comparison.

11. The method of claim 7 wherein the arrival time of the QRS complex is determined based on one of a real-time data and a stored data.

12. The method of claim 7, further comprising the step of: removing a linear trend from instantaneous heart rates prior to determining an absolute deviation of the instantaneous heart rates compared to a mean of the instantaneous heart rates for each of the first number of segments.

* * * * *

UNITED STATES PATENT AND TRADEMARK OFFICE
CERTIFICATE OF CORRECTION

PATENT NO. : 7,630,756 B2  Page 1 of 1
APPLICATION NO. : 11/253375
DATED : December 8, 2009
INVENTOR(S) : D. T. Linker It is certified that error appears in the above-identified patent and that said Letters Patent is hereby corrected as shown below:

| COLUMN | LINE | ERROR |
|---|---|---|
| 15 | 59 | after "monitoring the electrical" insert --activity of a heart-- |
| 16 | 61 | after "segments" insert --;-- |
| 16 | 61 | the phrase "selecting the median value" should begin a new line |

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,630,756 B2 |
| APPLICATION NO. | : 11/253375 |
| DATED | : December 8, 2009 |
| INVENTOR(S) | : David Thor Linker |

It is certified that error appears in the above-identified patent and that said Letters Patent is hereby corrected as shown below:

Title page, item (*) Notice: should read as follows:

Subject to any disclaimer, the term of this patent is extended or adjusted under 35 U.S.C. 154(b) by 741 days.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,630,756 B2 | Page 1 of 1 |
| APPLICATION NO. | : 11/253375 | |
| DATED | : December 8, 2009 | |
| INVENTOR(S) | : David Thor Linker | |

It is certified that error appears in the above-identified patent and that said Letters Patent is hereby corrected as shown below:

Title page, item (*) Notice: should read as follows:

Subject to any disclaimer, the term of this patent is extended or adjusted under 35 U.S.C. 154(b) by 783 days.

This certificate supersedes the Certificate of Correction issued June 22, 2010.

Signed and Sealed this

Twentieth Day of July, 2010

David J. Kappos
*Director of the United States Patent and Trademark Office*